United States Patent
Wurziger et al.

(10) Patent No.: US 6,921,829 B2
(45) Date of Patent: Jul. 26, 2005

(54) METHOD FOR FORMULATING ORGANIC COMPOUNDS

(75) Inventors: Hanns Wurziger, Darmstadt (DE); Guido Pieper, Mannheim (DE); Norbert Schwesinger, Eching (DE)

(73) Assignee: Merck Patent GmbH, Darmstadt (DE)

( * ) Notice: Subject to any disclaimer, the term of this patent is extended or adjusted under 35 U.S.C. 154(b) by 4 days.

(21) Appl. No.: 10/296,459
(22) PCT Filed: May 28, 2001
(86) PCT No.: PCT/EP01/06043
§ 371 (c)(1), (2), (4) Date: Nov. 25, 2002
(87) PCT Pub. No.: WO01/92187
PCT Pub. Date: Dec. 6, 2001

(65) Prior Publication Data
US 2003/0139630 A1 Jul. 24, 2003

(30) Foreign Application Priority Data
May 29, 2000 (DE) .......................................... 100 26 645

(51) Int. Cl.$^7$ ........................ G07D 209/12; C07B 41/06
(52) U.S. Cl. ...................................... 548/469; 568/451
(58) Field of Search ......................................... 548/469

(56) References Cited

U.S. PATENT DOCUMENTS 5,811,062 A * 9/1998 Wegeng et al. ............. 422/129

FOREIGN PATENT DOCUMENTS

WO      WO 99/22857    *  5/1999

* cited by examiner

Primary Examiner—Kamal A. Saeed
(74) Attorney, Agent, or Firm—Millen White Zelano & Branigan, P.C.

(57) ABSTRACT

The invention generally relates to a method of formylating organic compounds in a microreactor.

50 Claims, No Drawings

METHOD FOR FORMULATING ORGANIC COMPOUNDS

The present invention relates to a process for the formylation of organic compounds.

The formylation of suitable organic compounds is a process which is very frequently carried out in the chemical industry and whose great importance is also reflected in numerous publications on this subject.

However, carrying out formylations on an industrial scale is accompanied by safety problems and risks. Firstly, relatively large amounts of highly toxic chemical substances which themselves pose a considerable risk to human beings and the environment are frequently used and, secondly, formylations frequently proceed very exothermically so that there is an increased risk of explosion when carrying out these reactions on an industrial scale. Obtaining approval from the authorities under the German Federal Pollution Control Law for the operation of plants for the formylation of organic compounds on an industrial scale is therefore associated with a considerable outlay.

It is therefore an object of the present invention to provide a process for the formylation of organic compounds which avoids the abovementioned disadvantages. This process should, in particular, be able to be carried out in a simple, reproducible manner with increased safety for human beings and the environment and give good yields, and the reaction conditions should be very readily controllable.

This object is surprisingly achieved by the process of the invention for the formylation of organic compounds, in which at least one organic compound in liquid or dissolved form is mixed with at least one formylation reagent in liquid or dissolved form in at least one microreactor, reacts during a residence time and the formylated organic compound is, if desired, isolated from the reaction mixture.

For the purposes of the present invention, a formylation is a reaction in which an aldehyde group and/or a keto group is/are introduced into an organic compound.

Advantageous embodiments of the process of the invention are described in the subordinate claims.

According to the invention, individual organic compounds or mixtures of at least two of these compounds can be reacted by the process claimed. Preference is given to reacting only one organic compound by the process of the invention.

For the purposes of the invention, a microreactor is a reactor having a volume of $\leq 1000$ μl in which the liquids and/or solutions are intimately mixed at least once. The volume of the microreactor is preferably $\leq 100$ μl, particularly preferably $\leq 50$ μl.

The microreactor is preferably made of thin, interconnected silicon structures.

The microreactor is preferably a miniaturized flow reactor, particularly preferably a static micromixer. The microreactor is very particularly preferably a static micromixer as described in the Patent Application WO 96/30113, which is hereby incorporated by reference into the present disclosure. Such a micromixer has small channels in which liquids and/or chemical compounds present in solutions are mixed with one another by means of the kinetic energy of the flowing liquids and/or solutions.

The channels of the microreactor preferably have a diameter of from 10 to 1000 μm, particularly preferably from 20 to 800 μm and very particularly preferably from 30 to 400 μm.

The liquids and/or solutions are preferably pumped into the microreactor so that they flow through the latter at a flow rate of from 0.01 μl/min to 100 ml/min, particularly preferably from 1 μl/min to 1 ml/min.

According to the invention, the microreactor can preferably be heated and cooled.

The microreactor is, according to the invention, preferably connected via an output to at least one residence section, preferably a capillary, particularly preferably a heatable/coolable capillary. After they have been mixed in the microreactor, the liquids and/or solutions are passed through this residence section or capillary to increase their residence time.

For the purposes of the invention, the residence time is the time between the mixing of the starting materials and the work-up of the resulting reaction solution for analysis or isolation of the desired product(s).

The residence time necessary in the process of the invention depends on various parameters such as the temperature or the reactivity of the starting materials. A person skilled in the art can match the residence time to these parameters and thus achieve optimized reaction conditions.

The residence time of the reaction solution in the system employed comprising at least one microreactor and, if desired, one residence section can be set by choice of the flow rate of the liquids and/or solutions used.

It is likewise preferred for the reaction mixture to be passed through two or more microreactors connected in series. This increases the residence time even in the case of an increased flow rate and results in the components used in the formylation reaction being reacted so that an optimum product yield of the desired formylated organic compound (s) is achieved.

In a further, preferred embodiment, the reaction mixture is passed through two or more microreactors connected in parallel so as to increase the throughput.

In another preferred embodiment of the process of the invention, the number and arrangement of the channels is varied in one or more microreactor(s) so as to increase the residence time, so that an optimum yield of the desired formylated organic compound(s) is also achieved here at an increased flow rate.

The residence time of the reaction solution in the microreactor or if applicable in the microreactor and the residence section is preferably $\leq 15$ hours, preferably $\leq 3$ hours, particularly preferably $\leq 1$ hour.

The process of the invention can be carried out within a very wide temperature range which is limited essentially by the temperature stability of the materials used for the construction of the microreactor, any residence section and further components such as connections and seals and by the physical properties of the solutions and/or liquids used. The process of the invention is preferably carried out at a temperature of from −100 to +250° C., preferably from −78 to +150° C., particularly preferably from 0 to +100° C.

The process of the invention can be carried out either continuously or batchwise. It is preferably carried out continuously.

To carry out the process of the invention for the formylation of organic compounds, it is necessary for the formylation reaction to be carried out, if possible, in a homogeneous liquid phase containing no solid particles or only very small solid particles, since otherwise the channels in the microreactors become blocked.

The course of the formylation reaction in the process of the invention can be followed by means of various analytical methods known to those skilled in the art and if necessary regulated. The course of the reaction is preferably followed chromatographically, particularly preferably by high-pressure liquid chromatography, and regulated if necessary. The control of the reaction is significantly improved compared with known processes.

After the reaction, the formylated organic compound(s) is (are) isolated if desired. The formylated organic compound(s) is (are) preferably isolated from the reaction mixture by extraction.

As organic compounds, it is possible for all organic compounds known to those skilled in the art as substrates for formylations to be used in the process of the invention. The organic compounds are preferably selected from among olefins, alkynes, aromatic compounds, heteroaromatic compounds, transition metal complexes, CH-acid compounds, enamides and mixtures of at least two of these compounds.

As olefins, it is possible to use all olefins known to those skilled in the art which are suitable as substrates for formulations. These encompass straight-chain, branched and cyclic olefins. Preference is given to using unsubstituted or substituted ethylene as olefin.

As alkynes, it is possible to use all alkynes known to those skilled in the art which are suitable as substrates for formylations. These encompass straight-chain, branched and cyclic alkynes. Preference is given to using substituted acetylene as alkyne.

As aromatic compounds, it is possible to use all aromatic compounds known to those skilled in the art which are suitable as substrates for formulations. For the purposes of the invention, these include compounds and/or derivatives which have a monocyclic and/or polycyclic homoaromatic framework or a corresponding substructure, e.g. in the form of substituents. As aromatic compound, which may be substituted or unsubstituted, preference is given to using azulene, indole, phenol, an aromatic amine or a mixture of at least two of these compounds.

As heteroaromatic compounds, it is possible to use all heteroaromatic compounds known to those skilled in the art which are suitable as substrates for formylations and have at least one heteroatom. For the purposes of the invention, heteroaromatic compounds include heteroaromatic compounds and/or their derivatives which have at least one monocyclic and/or polycyclic heteroaromatic framework or a corresponding substructure, e.g. in the form of substituents. These heteroaromatic frameworks or substructures preferably include at least one oxygen, nitrogen and/or sulfur atom. As heteroaromatic compounds, which may be substituted or unsubstituted, particularly preference is given to using furan, thiophene, pyrrole, benzofuran, benzothiophene, pyrazole, imidazole, thiazole, oxazole, pyrimidine, porphyrin, hydantoin, thiohydantoin, imidazolone, pyrazolone or a mixture of at least two of these compounds.

As transition metal complexes, it is possible to use all transition metal complexes known to those skilled in the art which are suitable as substrates or formylations. For the purposes of the invention, transition metal complexes include, inter alia, metallocene compounds, preferably ferrocene, and carbonyl compounds of the transition metals, preferably carbonyl compounds of iron, chromium or manganese and mixtures of at least two of these compounds.

As CH-acid compounds, it is possible to use all CH-acid compounds known to those skilled in the art which are suitable as substrates for formylations and have at least one acid proton in the $\alpha$ position relative to a carbonyl group. As CH-acid compound, preference is given to using an enol, an enol ether, a $\beta$-keto compound, particularly preferably pyrazole-3,5-dione, or a mixture of at least two of these compounds.

As enamides, it is possible to use all enamides known to those skilled in the art which are suitable as substrates for formylations. As enamide, preference is given to using a vinylic formamide, particularly preferably 3-dimethylaminopropenal.

Formylation reagents which can be used in the process of the invention are all formylation reagents known to those skilled in the art which are suitable for formylations and mixtures of at least two of these reagents. Preference is given to using only one formulation reagent in each case. For the purposes of the invention, formulation reagents also include formylation reagents formed in situ, i.e. formylation reagents which are formed immediately before or during the formylation reaction.

In a further, preferred embodiment of the invention, the formulation reagent used is an N,N-disubstituted formamide, an N-alkylformanilide, an N,N-disubstituted amide or a mixture of at least two of these compounds in the presence of an inorganic acid chloride, an inorganic ester, an acid anhydride, an adduct of triphenylphosphine and bromine, cyanuric chloride, hexachlorocyclotriphosphazane or a mixture of at least two of the abovementioned compounds.

As N,N-disubstituted formamide, preference is given to using an N-aryl-N-alkylformamide, particularly preferably N-phenyl-N-methylformamide, an N,N-dialkyl formamide, particularly preferably N,N-dimethylformamide, a vinylic N,N-dialkylformamide or a mixture of at least two of these compounds.

As N-alkylformanilide, preference is given to using an N-methylformamide.

As N,N-disubstituted amide, preference is given to using an N,N-dialkylacetamide, particularly preferably N,N-dimethylacetamide, an N,N-dialkyl propionamide, particularly preferably N,N-dimethylpropionamide, an N,N-dialkylbenzamide, preferably N,N-dimethylbenzamide, or a mixture of at least two of these compounds.

As inorganic acid chloride, preference is given to using phosphorus oxychloride, thionyl chloride, phosgene, a phosgene substitute, in particular diphosgene or triphosgene, pyrophosphoryl chloride, oxalyl chloride, sulfuryl chloride, benzoyl bromide or a mixture of at least two of these compounds.

As acid anhydride, preference is given to using trifluoromethanesulfonic anhydride.

As inorganic ester, preference is given to using a dialkyl sulfate, particularly preferably dimethyl sulfate.

The molar ratio of N,N-disubstituted formamide and/or N-alkylformanilide and/or N,N-disubstituted amide to inorganic acid chloride and/or inorganic ester and/or acid anhydride is preferably equimolar. Furthermore, the acid chloride and/or the inorganic ester and/or the acid anhydride is/are preferably present in a 2-fold to 10-fold molar excess, particularly preferably in a 3-fold to 5-fold molar excess, based on the N,N-disubstituted formamide and/or the N-alkylformanilide and/or the N,N-disubstituted amide.

In a further, preferred embodiment of the process of the invention, the formylation reagent used is zinc(II) cyanide in the presence of a protic acid, preferably hydrochloric acid.

The molar ratio of organic compound to formylation reagent used in the process of the invention depends on the reactivity of the organic compound used and the reactivity of the formylation reagent used. The formylation reagent and the organic compound are preferably used in an equimolar ratio. In another preferred embodiment of the process of the invention, the formylation reagent is used in a 2-fold to 20-fold molar excess, particularly preferably in a 3-fold to 15-fold excess, very particularly preferably in a 4-fold to 10-fold excess, based on the organic compound.

The selectivity of the reaction itself depends not only on the concentration of the reagents used but also on a series of further parameters such as the temperature, the type of formylation reagent used or the residence time. A person skilled in the art will be able to match the various parameters to the respective formylation so that the desired formylation product(s) is (are) obtained.

It is important for the process of the invention that the organic compounds used and the formylation reagents used are either themselves liquid or are in dissolved form. If they are themselves liquid, they can, if desired, also be used as solvents for further components of the formylation reaction. If the organic compounds or formylation reagents used are not themselves in liquid form, they have to be dissolved in a suitable solvent before carrying out the process of the invention. Solvents used are preferably halogenated solvents, particularly preferably dichloromethane, chloroform, 1,2-dichloroethane or 1,1,2,2-tetrachloroethane, straight-chain, branched or cyclic paraffins, particularly preferably pentane, hexane, heptane, octane, cyclopentane, cyclohexane, cycloheptane or cyclooctane, or straight-chain, branched or cyclic ethers, particularly preferably diethyl ether, methyl tert-butyl ether, tetrahydrofuran or dioxane, aromatic solvents, particularly preferably toluene, xylenes, ligroin or phenyl ether, N-containing solvents, particularly preferably N,N-dimethylformamide or N-methylpyrrolidone, or mixtures of at least two of the abovementioned solvents.

In the process of the invention, the danger to human beings and the environment due to loss of containment of chemicals is considerably reduced and thus leads to increased safety when handling hazardous substances. Furthermore, the formylation of organic compounds by the process of the invention makes it possible for the reaction conditions, e.g. reaction time and reaction temperature, to be controlled better than is possible in the conventional processes. In addition, the risk of explosions in the case of very strongly exothermic formulations is significantly reduced in the process of the invention. The temperature can be selected individually and kept constant in each volume element of the system. In the process of the invention, the formylation reactions are very fast and can be regulated precisely. The formylated organic compounds can thus be obtained in very good and reproducible yields.

It is also particularly advantageous that the process of the invention can be carried out continuously. As a result, it is faster and cheaper than conventional processes and it is possible to prepare any amounts of the formylated organic compounds without a great outlay in terms of instrumentation.

The invention is illustrated below by means of an example. This example serves merely to illustrate the invention and does not restrict its scope.

EXAMPLE

Formylation of Indole to Give indole-3-carboxaldehyde

The formylation of indole by means of N,N-dimethylformamide in the presence of phosphorus oxychloride was carried out in a static micromixer (Technische Universität Ilmenau, Fakultät Maschinenbau, Dr.-Ing. Norbert Schwesinger, Postfach 100565, D-98684, Ilmenau) having a size of 40 mm×25 mm×1 mm and a total of 11 mixing stages each having a volume of 0.125 µl. The total pressure drop was about 1000 Pa. The static micromixer was connected via an outlet and an Omnifit intermediate-pressure HPLC connector (Omnifit, Great Britain) to a Teflon capillary having an internal diameter of 0.49 mm and a length of 1.0 m. The reaction was carried out at 0° C. and 25° C. The static micromixer and the Teflon capillary were for this purpose maintained at the respective temperature in a thermostated double-walled vessel.

A 2 ml disposable syringe was filled with part of a solution of 0.78 ml (8.5 mmol) of phosphorus oxychloride and 20 ml of N,N-dimethylformamide, which simultaneously serves as solvent, and a further 2 ml disposable syringe was filled with part of a solution of 1 g (8.5 mmol) of indole in 20 ml of N,N-dimethylformamide. The contents of both syringes were subsequently transferred by means of a metering pump (Harvard Apparatus Inc., Pump 22, South Natick, Mass., USA) into the static micromixer. Before carrying out the reaction, the test apparatus was calibrated to determine the dependence of the residence time on the pump flow rate. The residence time was set to 1.88; 3.75; 7.5; 15 and 30 minutes. The reactions were followed with the aid of a Merck Hitachi LaChrom HPLC instrument. The ratio of starting material to product corresponding to the respective reaction conditions and residence times was also determined by means of HPLC on the abovementioned instrument.

What is claimed is:

1. A process for the formylation of at least one organic compound, comprising mixing the at least one organic compound in liquid or dissolved form with at least one formylation reagent in liquid or dissolved form in at least one microreactor, reacting during a residence time and optionally isolating a formylated organic compound from the reaction mixture.

2. A process according to claim 1, wherein the microreactor is a miniaturized flow reactor.

3. A process according to claim 1, wherein the microreactor is a static micromixer.

4. A process according to claim 1, wherein the microreactor is connected via an outlet to a capillary, which can be heated and cooled.

5. A process according to claim 1, wherein the volume of the microreactor is $\leq$ about 100 µl.

6. A process according to claim 1, wherein the microreactor can be heated and cooled.

7. A process according to claim 1, wherein the microreactor has channels having a diameter of about 10–about 1000 µm.

8. A process according to claim 1, wherein the reaction mixture flows through the microreactor at a flow rate of about 0.01 ml/min.–about 100 ml/min.

9. A process according to claim 1, wherein the residence time of the compounds used in the microreactor or in the microreactor and the capillary is $\leq$ about 15 hours.

10. A process according to claim 1, wherein the process is carried out at a temperature of about −100–about +250° C.

11. A process according to claim 1, further comprising chromatography after the reaction.

12. A process according to claim 1, wherein the formylated organic compound is isolated from the reaction mixture by extraction.

13. A process according to claim 1, wherein the formylation reagent is an N,N-disubstituted formamide, an N-alkylformanilide, an N,N-disubstituted amide or a mixture of at least two of these compounds in the presence of an inorganic acid chloride, an inorganic ester, an acid anhydride, an adduct of triphenylphosphine and bromine, cyanuric chloride, hexachlorocyclophosphazane or a mixture of at least two of these compounds.

14. A process according to claim 13, wherein the formulation reagent is at least one N,N-disubstituted formamide, which is an N-aryl-N-alkylformamide, an N,N-dialkylformamide, a vinylic N,N-dialkylformamide or a mixture of at least two of these compounds.

15. A process according to claim 13, wherein the formylation reagent is the N-alkylformanilide, which in turn is N-methylformamide.

16. A process according to claim 13, wherein the formylation reagent is at least one N,N-disubstituted amide, which in turn is an N,N-dialkylacetamide, an N,N-dialkyl propionamide, an N,N-dialkylbenzamide, or a mixture of at least two of these compounds.

17. A process according to claim 13, wherein the formylation reagent is at least one inorganic acid chloride, which in turn is phosphorus oxychloride, thionyl chloride, phosgene, a phosgene substitute, pyrophosphoryl chloride, oxalyl chloride, sulfuryl chloride, benzoyl chloride or a mixture of at least two of these acid chlorides.

18. A process according to claim 13, wherein the formylation reagent is the inorganic ester, which in turn is a dialkyl sulfate.

19. A process according to claim 13, wherein the formylation reagent is the acid anhydride of trifluoromethanesulfonic anhydride.

20. A process according to claim 13, wherein the molar ratio of the N,N-disubstituted formamide and/or the N-alkylformanilide and/or the N N-disubstituted amide to inorganic acid chloride and/or the inorganic ester and/or the acid anhydride is equimolar, or the inorganic acid chloride and/or the inorganic ester and/or the acid anhydride is/are used in a about 2-fold–about 10-fold polar excess, based on the N,N-disubstituted formamide and/or the N-alkylformanilide and/or the N,N-disubstituted amide.

21. A process according to claim 1, wherein the formylation reagent is zinc(II) cyanide in the presence of a protic acid.

22. A process according to claim 1, wherein the at least one organic compound used is an olefin, an alkyne, an aromatic compound, a heteroaromatic compound, a transition metal complex, a CH-acid compound, an enamide or a mixture of at least two of these compounds.

23. A process according to claim 22, wherein the at least one organic compound is the olefin, which is an unsubstituted or a substituted ethylene.

24. A process according to claim 22, wherein the at least one organic compound is the alkyne of an unsubstituted or a substituted acetylene.

25. A process according to claim 22, wherein the at least one organic compound is the aromatic compound, optionally substituted, of an azulene, indole, phenol, an aromatic amine or a mixture of at least two of these compounds.

26. A process according to claim 22, wherein the at least one organic compound is the transition metal complex of a metallocene, a carbonyl compound of a transition metal, or a mixture of at least two of these compounds.

27. A process according to claim 22, wherein the at least one organic compound is the heteroaromatic compound, optionally substituted, of a furan, thiophene, pyrrole, benzofuran, benzothiophene, pyrazole, imidazole, thiazole, oxazole, pyrimidine, porphyrin, hydantoin, thiohydantoin, imidazolone, pyrazolone or a mixture of at least two of these compounds.

28. A process according to claim 22, wherein the at least one organic compound is the CH-acid compound of an enol, an enol ether or a β-keto compound, or a mixture of at least two of these compounds.

29. A process according to claim 22, wherein the at least one organic compound is a vinylic formamide.

30. A process according to claim 1, wherein the molar ratio of the organic compound to the formylation reagent is equimolar, or the formylation reagent is used in a about 2-fold–about 20-fold molar excess, based on the organic compound.

31. A process according to claim 26, wherein the transition metal complex is a metallocene, which in turn is a ferrocene.

32. A process according to claim 26, wherein the transition metal complex is the carbonyl compound of the transition metal, which in turn is an iron, chromium or a manganese carbonyl compound.

33. A process according to claim 1, wherein the volume of the microreactor is ≦about 50 μl.

34. A process according to claim 1, wherein the microreactor has channels having a diameter of about 20–about 800 μl.

35. A process according to claim 1, wherein the microreactor has channels having a diameter of about 30–about 400 μl.

36. A process according to claim 1, wherein the reaction mixture flows through the microreactor at a flow rate of about 1 μl/min–about 1 ml/min.

37. A process according to claim 1, wherein the residence time of the compounds used in the microreactor or in the microreactor and the capillary is ≦about 3 hours.

38. A process according to claim 1, wherein the residence time of the compounds used in the microreactor or in the microreactor and the capillary is ≦about 1 hour.

39. A process according to claim 1, wherein the process is carried out at a temperature of about −78–about +150° C.

40. A process according to claim 1, wherein the process is carried out at a temperature of about 0–+about 100° C.

41. A process according to claim 13, wherein the formylation reagent is at least one N,N-disubstituted amide, which in turn is N,N-dimethylacetamide, N,N-dimethylpropionamide, N,N-dimethylbenzamide, or a mixture of at least two of these compounds.

42. A process according to claim 17, wherein the phosgene substitute is diphosgene or triphosgene.

43. A process according to claim 20, wherein the inorganic acid chloride and/or inorganic ester and/or acid anhydride is/are used in about 3-fold–about a 5-fold molar excess, based on the N,N-disubstituted formamide and/or the N-alkyl formanilide and/or the N,N-disubstituted amide.

44. A process according to claim 1, wherein the molar ratio of the organic compound to formylation reagent is equimolar, or the formylation reagent is used in about a 3-fold–about a 15-fold molar excess based on the organic compound.

45. A process according to claim 1, wherein the molar ratio of the organic compound to formylation reagent is equimolar, or the formylation reagent is used in about a 4-fold–about a 10-fold molar excess based on the organic compound.

46. A process according to claim 1, wherein the at least one organic compound is indole.

47. A process according to claim 1, wherein the at least one organic compound is indole and the formylation reagent is N,N-dimethylformamide in the presence of a phosphorus oxychloride.

48. A process according to claim 18, wherein the dialkyl sulfate is dimethyl sulfate.

49. A process according to claim 13, wherein the formylation reagent is an N-phenyl-N-methylformamide, or an N,N-dimethylformamide.

50. A process according to claim 11, wherein the chromatography is a high-pressure liquid chromatography, and the reaction is regulated.

* * * * *

UNITED STATES PATENT AND TRADEMARK OFFICE
CERTIFICATE OF CORRECTION

PATENT NO. : 6,921,829 B2
DATED : July 26, 2005
INVENTOR(S) : Hanns Wurgziger et al.

It is certified that error appears in the above-identified patent and that said Letters Patent is hereby corrected as shown below:

Column 7,
Line 8, "N-methylformamide" should read -- N-methylformanilide --.
Line 27, "inorganic acid chloride" should read -- the inorganic acid chloride --.
Line 37, "compound used is an olefin" should read -- compound is an olefin --.

Column 8,
Line 56, "phosphorus" should read -- phosphorous --.

Signed and Sealed this

Fourth Day of October , 2005

JON W. DUDAS
*Director of the United States Patent and Trademark Office*